(12) United States Patent
Alshemari

(10) Patent No.: US 10,188,416 B2
(45) Date of Patent: Jan. 29, 2019

(54) BIFURCATED FORCEPS

(71) Applicant: Hasan Alshemari, Safat (KW)

(72) Inventor: Hasan Alshemari, Safat (KW)

( * ) Notice: Subject to any disclaimer, the term of this patent is extended or adjusted under 35 U.S.C. 154(b) by 8 days.

(21) Appl. No.: 15/801,206

(22) Filed: Nov. 1, 2017

(65) Prior Publication Data

US 2018/0064459 A1    Mar. 8, 2018

Related U.S. Application Data

(63) Continuation-in-part of application No. 15/658,142, filed on Jul. 24, 2017, which is a continuation of application No. 15/404,173, filed on Jan. 11, 2017, now abandoned.

(60) Provisional application No. 62/276,963, filed on Jan. 11, 2016.

(51) Int. Cl.
   *A61B 17/30*      (2006.01)
(52) U.S. Cl.
   CPC ........ *A61B 17/30* (2013.01); *A61B 2017/303* (2013.01)
(58) Field of Classification Search
   CPC . A61B 17/30; A61B 17/22031; A61B 17/282; A61B 17/29; A61B 2017/303; A61B 2017/1125; A61B 2017/2906; A61B 2017/2926; A61B 18/1442–18/1447; A61B 2018/1462; A61B 10/06; A61B 17/1606–17/1611; A61B 17/28–2017/308; A61B 17/22032–2017/22035; A61B 17/44–2017/447; B25B 9/02; B25B 7/02

USPC .......................... 81/303; 294/99.2, 104, 106
See application file for complete search history.

(56) References Cited

U.S. PATENT DOCUMENTS

| | | | | |
|---|---|---|---|---|
| 1,539,526 | A | * 5/1925 | Swickard | .................. B25B 7/00 81/303 |
| 2,430,544 | A | * 11/1947 | Walker | ............... H01H 85/0208 294/118 |
| 4,610,252 | A | * 9/1986 | Catalano | ................. A61B 17/30 606/157 |
| 5,019,091 | A | 5/1991 | Porat et al. | |
| 5,059,198 | A | * 10/1991 | Gimpelson | .......... A61B 17/282 606/119 |
| 5,284,162 | A | * 2/1994 | Wilk | ...................... A61B 17/29 128/898 |
| 5,336,228 | A | * 8/1994 | Cholhan | ............ A61B 17/2812 606/119 |

(Continued)

*Primary Examiner* — Ryan J Severson
*Assistant Examiner* — Charles Wei
(74) *Attorney, Agent, or Firm* — Richard C. Litman

(57) ABSTRACT

The bifurcated forceps include a first pair of forceps having a first pair of opposed forceps or pincer arms and a second pair of opposed forceps or pincer arms. Each arm has a pivot end and a gripping end. Each pair is coupled at the pivot end and resiliently biased to a spaced apart position at the gripping end so that each pair may be independently pinched together, defining a gripping plane. The pivot ends of the two pairs are rotatable about a common pivot axis in a plane normal to the gripping planes, the arms in each pair being constrained to rotate to an identical radial angle in order to grip the same object at spaced apart positions. Adjacent arms in different pairs may have a mating blade and receptacle configuration to releasably lock the arms together to use the two pairs as a single pair.

15 Claims, 4 Drawing Sheets

(56) References Cited

U.S. PATENT DOCUMENTS

| | | | | |
|---|---|---|---|---|
| 5,665,100 A | * | 9/1997 | Yoon | A61B 10/06 |
| | | | | 606/139 |
| 5,776,075 A | * | 7/1998 | Palmer | A61B 10/06 |
| | | | | 600/564 |
| 5,997,567 A | * | 12/1999 | Cangelosi | A61B 17/04 |
| | | | | 294/99.2 |
| 6,863,679 B1 | * | 3/2005 | Aaron | A61B 17/30 |
| | | | | 606/206 |
| 7,226,465 B1 | * | 6/2007 | Farin | A61B 18/1445 |
| | | | | 606/205 |
| 7,625,028 B2 | * | 12/2009 | Cho | B25B 9/02 |
| | | | | 294/99.2 |
| 7,641,248 B2 | * | 1/2010 | Cho | A61B 17/30 |
| | | | | 294/99.2 |
| 8,529,580 B1 | * | 9/2013 | Alshemari | A61B 17/29 |
| | | | | 606/109 |
| 8,608,774 B1 | * | 12/2013 | Alshemari | A61B 17/30 |
| | | | | 606/210 |
| 2007/0118174 A1 | * | 5/2007 | Chu | A61B 17/0401 |
| | | | | 606/207 |
| 2008/0125810 A1 | | 5/2008 | Cho | |
| 2011/0301604 A1 | * | 12/2011 | Horner | A61B 17/29 |
| | | | | 606/52 |
| 2013/0085494 A1 | * | 4/2013 | Weisenburgh, II | |
| | | | | A61B 17/0469 |
| | | | | 606/41 |
| 2014/0012314 A1 | * | 1/2014 | Dai | A61B 17/2804 |
| | | | | 606/207 |
| 2017/0273704 A1 | * | 9/2017 | Kaifeng | A61B 17/30 |

* cited by examiner

BIFURCATED FORCEPS

CROSS-REFERENCE TO RELATED APPLICATIONS

This is a continuation-in-part of my prior U.S. patent application Ser. No. 15/658,142, filed on Jul. 24, 2017, which is a continuation of my prior U.S. patent application Ser. No. 15/404,173, filed on Jan. 11, 2017, now abandoned, which claimed priority to U.S. provisional patent application Ser. No. 62/276,963, filed Jan. 11, 2016.

BACKGROUND

1. Field

The disclosure of the present patent application relates to gripping instruments, and particularly to bifurcated forceps having two pairs of pincer arms pivotally attached to each other so that they may be collapsed together to function as a single forceps or rotated to separate the pairs in order to simultaneously grip an elongated or broad object with forceps at two spaced apart locations using a single hand to operate the forceps.

2. Description of the Related Art

Common forceps are designed to have a single pair of pincer arms, which extend from a rear connection point and terminate at the same relative position. This allows for an object to be gripped between the terminal ends of each pincer arm. Generally the terminal end of each pincer arm includes a fine point or pad or a serrated jaw to allow for delicate manipulation or firm gripping of objects. The terminal ends can be of any shape or size. Further, the terminal ends may have different gripping geometry to allow for gripping difficult or slippery objects. Common applications for these types of forceps include but are not limited to medical gripping, sport fishing, and cosmetics. However, if an instance arises where an object must be gripped at two locations, such as for stabilization of tissue, a second set of forceps must be used, which requires a second hand, which may be from the first user or from another individual.

Forceps have been designed which bifurcate the terminal ends into two sets of gripping points, which results in four terminal points from a common attachment point. The terminal ends are designed to contact in pairs such that upon the user pinching the device together, the two pairs of terminal ends contact the respective mate, allowing for two points of gripping. The primary downside to this design is that the sets of terminal ends are fixed in distance relative to each other, and usually are not spread very far apart. If a situation arises where a wider or shallower gripping distance is required, a different set of forceps would be required.

Thus, a bifurcated forceps solving the aforementioned problems is desired.

SUMMARY

The bifurcated forceps include a first pair of forceps having a first pair of opposed forceps or pincer arms and a second pair of opposed forceps or pincer arms. Each arm has a pivot end and a gripping end. Each pair is coupled at the pivot end and resiliently biased to a spaced apart position at the gripping end so that each pair may be independently pinched together, defining a gripping plane. The pivot ends of the two pairs are rotatable about a common pivot axis in a plane normal to the gripping planes, the arms in each pair being constrained to rotate to an identical radial angle in order to grip the same object at spaced apart positions. Adjacent arms in different pairs may have a mating blade and receptacle configuration to releasably lock the arms together to use the two pairs as a single pair.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
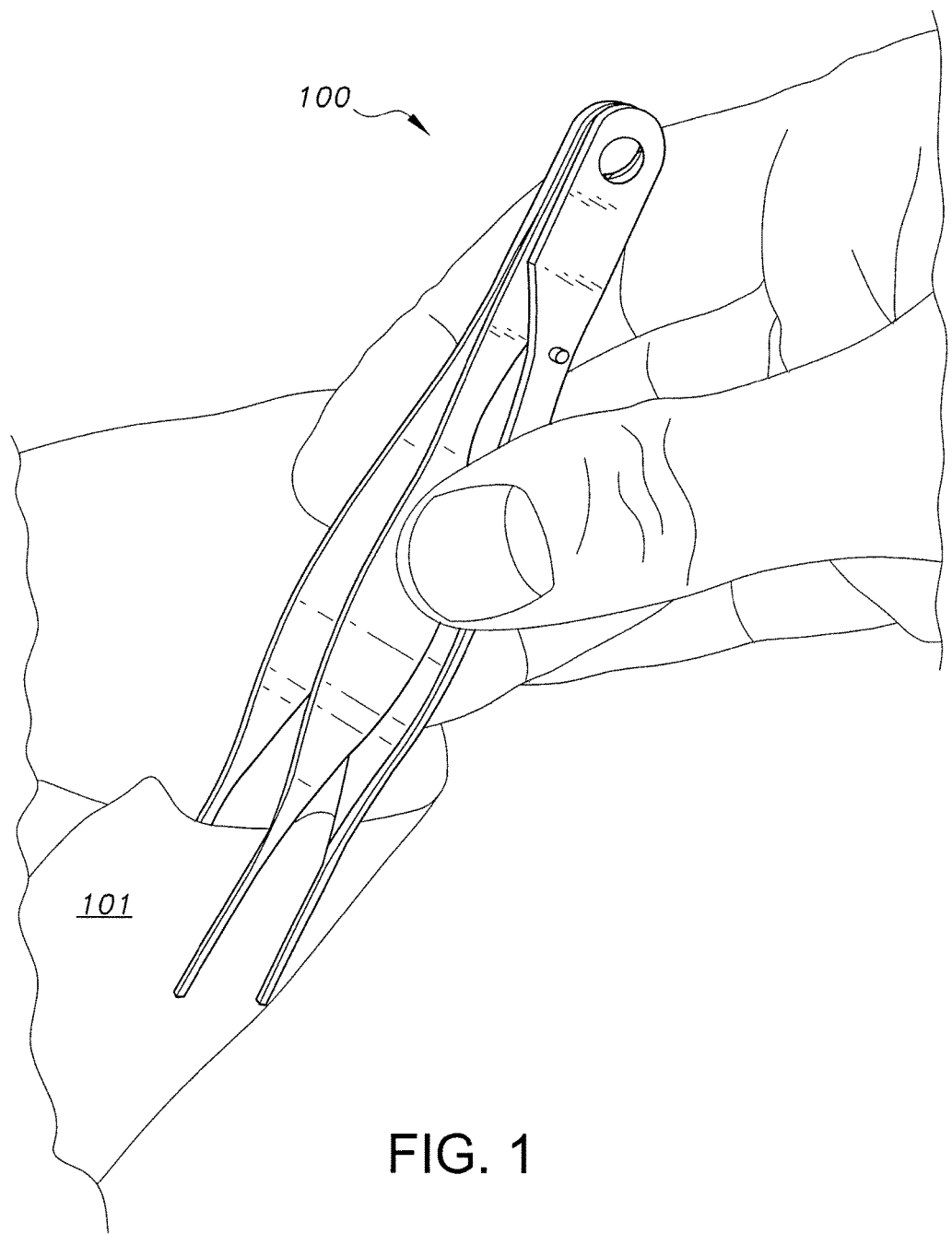
FIG. 1 is an environmental, perspective view of a bifurcated forceps, showing the two pairs of forceps spread apart to grasp a sheet at spaced apart locations.

The bifurcated forceps 100 is configured for allowing a user to grip wide or elongate objects at two spaced apart points, making it easier to manipulate the object without having the object rotate and providing a firmer grip by applying the pulling force at two spaced locations. It is to be noted that the term forceps encompasses any type of tweezer-like instrument, including a small pincer-like instrument having resiliently hinged, cooperating arms or jaw members particularly adapted or suited for plucking of handling small objects. FIG. 1 shows the bifurcated forceps 100 including two pairs of forceps rotated about a common pivot and spread apart to grasp a sheet 101 of tissue, paper, or the like at two spaced locations, providing a firmer grip for manipulating the sheet 101.

The bifurcated forceps 100 includes a first or outer pair of forceps 110 pivotally connected to a second or inner pair of forceps 120. The first pair of forceps 110 includes a first forceps arm 112 and a corresponding second forceps arm 114, each forceps arm 112, 114 of the outer pair of forceps 110 having a gripping end 116*a* and an opposing pivot end 116*b*. The first forceps arm 112 and the corresponding second forceps arm 114 of the outer pair of forceps 110 mirror one another and define a first gripping plane when the arms 112, 114 are squeezed towards each other to grip an object between the gripping ends 116*a*.

Likewise, the inner pair of forceps 120 includes a first forceps arm 122 and a corresponding second forceps arm 124, each forceps arm 122, 124 of the inner pair of forceps 120 having a gripping end 126a and an opposing pivot end 126b. Similar to the outer pair of forceps 110, the first forceps arm 122 and the corresponding second forceps arm 124 of the inner pair of forceps 120 mirror one another and define a second gripping plane when the arms 122, 124 are squeezed towards each other to grip an object between the gripping ends 126a.

Figure 2A:
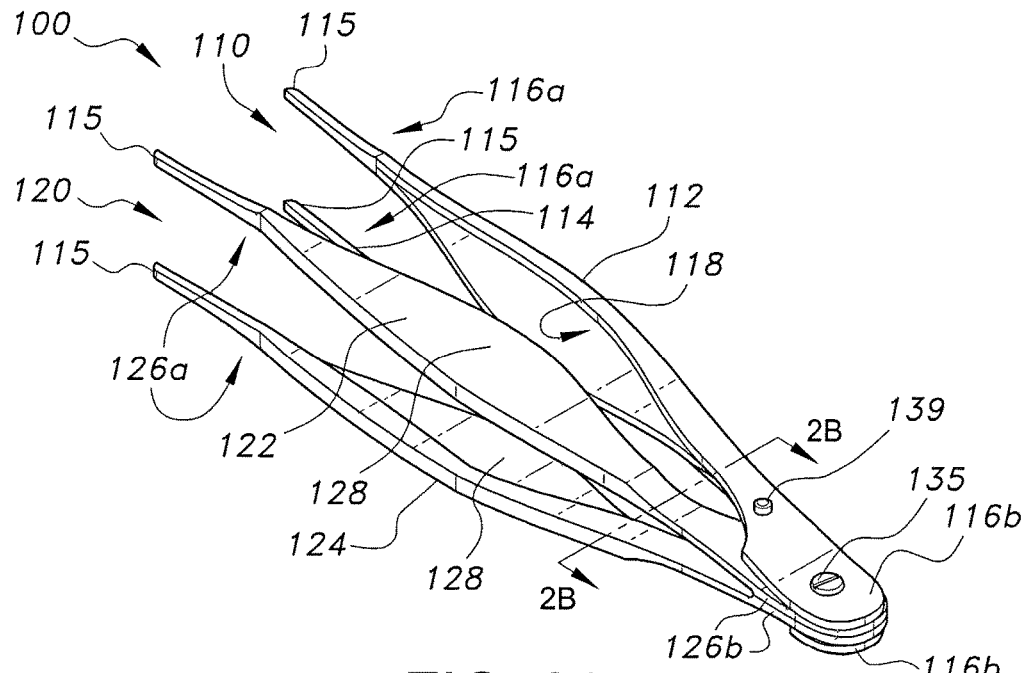
FIG. 2A is a perspective view of a first embodiment of bifurcated forceps shown in an open position, showing the two pairs of forceps spread apart, both arms of one pair having a blade configuration and both arms of the other pair having a receptacle configuration.
Figure 3:
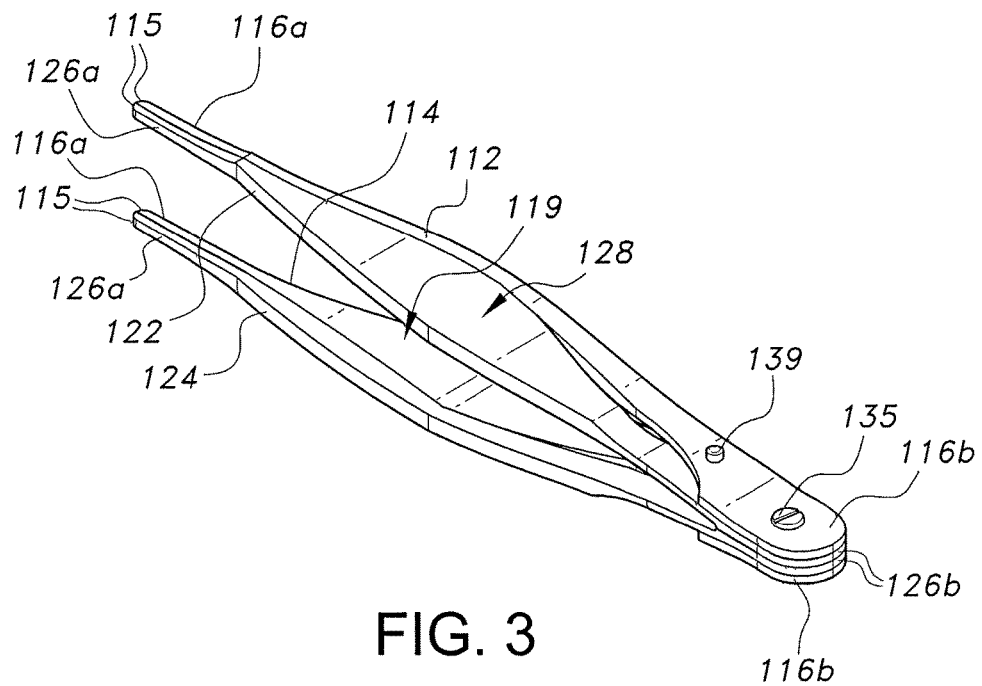
FIG. 3 is a perspective view of a bifurcated forceps, showing the two pairs locked together for use as a single forceps.
Figure 4:
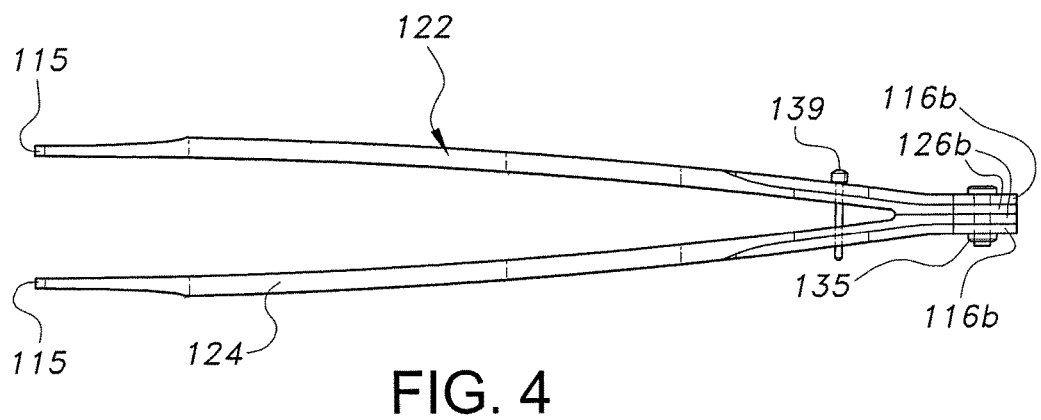
FIG. 4 is a side view of the bifurcated forceps.
Figure 5:
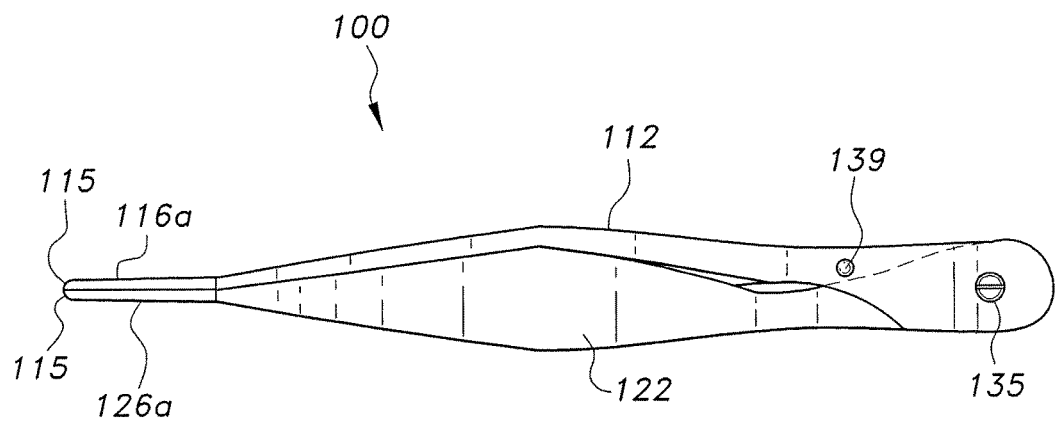
FIG. 5 is a top view of the bifurcated forceps, showing the two pairs locket together for use as a single pair of forceps.
Figure 6:
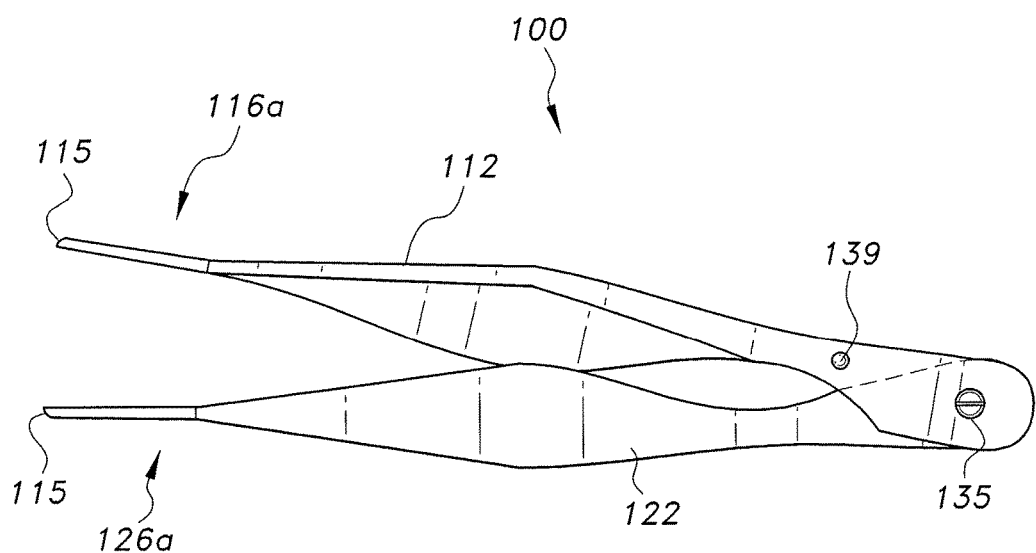
FIG. 6 is a top view of the bifurcated forceps, showing the two pairs for forceps spread apart for use as a double forceps.

The gripping end 116a, 126a of each forceps arm 112, 114, 122, 124 includes a corresponding gripping point 115, pad, or jaw such that when the one pair of forceps (e.g., the outer pair of forceps 110) is separated from the other pair of forceps (e.g., the inner pair of forceps 120), as discussed further below, there will be four gripping points 115 extending from the bifurcated forceps 100. The gripping points 115 are configured to grip an object, such as tissue, a suture needle, a fishing hook, etc. at a single point when the two pairs of forceps 110, 120 are locked together, as illustrated in FIGS. 3, 4, and 5, or at two different points when the two pairs of forceps 110, 120 are spread apart, as illustrated in FIGS. 1, 2A, 2C, and 6. Further, each of the forceps arms 112, 114, 122, 124 is of substantially the same length, and may be formed from any suitable type of flexible, medical grade material, such as stainless steel.

The pivot ends 116b of the forceps arms 112, 114 of the outer pair of forceps 110 and the pivot ends 126b of the forceps arms 122, 124 of the inner pair of forceps 120 are joined to each other by a pivot pin 135, such as a screw fastener, a rivet, or the like so that the outer pair of forceps 110 may be pivoted away from the inner pair of forceps 120 to a selective radial angle in a plane orthogonal to the gripping planes defined by squeezing the gripping ends 116a together and by squeezing the gripping ends 126a together. The forceps arms 112, 114 of the outer forceps 110 and the forceps arms 122, 124 of the inner forceps 120 are made of a resilient material, e.g., spring steel, resilient plastic, etc., such that the gripping ends 116a are biased to an open position and the gripping ends 126a are biased to an open position. When the forceps arms 112, 114 are squeezed towards each other to grip an object between the gripping ends 116a and then released, the gripping ends 116a resiliently return to a spaced apart open position. Similarly, when the forceps arms 122, 124 are squeezed towards each other to grip an object between the gripping ends 126a and then released, the gripping ends 126a resiliently return to a spaced apart open position.

Figure 2B:
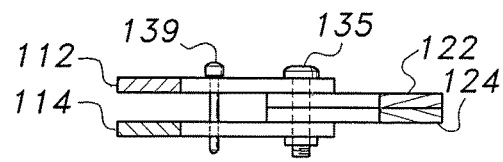
FIG. 2B is a section view drawn along lines 2B-2B of FIG. 2A.
Figure 2C:
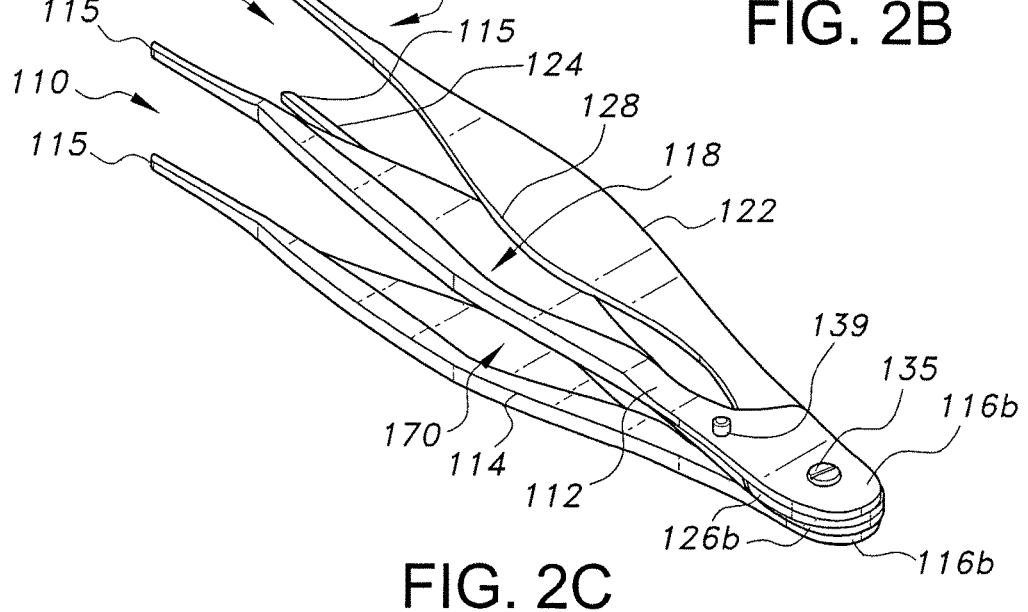
FIG. 2C is a perspective view of an alternative embodiment of a bifurcated forceps, showing the two pairs of forceps spread apart, the arms of the each pair having one arm in a blade configuration and the other arm in a receptacle configuration.

As shown in FIG. 2B, the pivot ends 126b of the inner forceps arms 122, 124 may be joined together by welding (metal welding or plastic welding, depending upon the material), adhesive, or any other joinery material or method known in the art so that when one arm 122, 124 is rotated around the pivot pin 135, the corresponding arm 122, 124 is constrained to rotate by an equal radial angle around the pivot pin 135, thus keeping the gripping ends 126a aligned. Similarly, the pivot ends 116b of the outer forceps arms 112, 114 are coupled or joined by any other joinery material or method known in the art so that when one arm 112, 114 is rotated around the pivot pin 135, the corresponding arm 112, 114 is constrained to rotate by an equal radial angle around the pivot pin 135, thus keeping the gripping ends 116a aligned. FIG. 2B shows and example of one way this may be done, viz., by a slider pin 139 extend through the outer forceps arms 112, 114 adjacent the pivot ends 116b, the arms 112,114 sliding towards and away from each other on the pin 139 as the arms 112, 114 are squeezed and released, while being constrained to rotate to a common radial angle about the pin 135 when the forceps 110, 120 are spread apart. It will be understood that the slider pin 139 is exemplary only, and any device or method (e.g., a common hub or sleeve disposed around the shaft of the pivot pin 135) for constraining the outer forceps arms 112, 114 to rotate to a common radial angle may be used.

As shown in FIG. 2A, in a first embodiment, the first outer forceps arm 112 and the second outer forceps arm 114 of the outer forceps 110 may both have a narrow fold defining a groove, pocket, or receptacle 118 facing the inner forceps 120 between the gripping end 116a and the pivot end 116b. The first inner forceps arm 122 and the second inner forceps arm 124 of the inner forceps 120 may both have an arcuate, thin blade edge 128 facing the outer forceps 110 between the gripping end 126a and the pivot end 126b so that when it is desired to use the bifurcated forceps 100 as a single forceps, the blades 128 snap into the receptacles 118 to temporarily lock the arms 112 and 122 together and to temporarily lock the arms 114 and 124 together so that the bifurcated forceps 100 may be used as a single forceps, as shown in FIGS. 3, 4, and 5. In a second embodiment, shown in FIG. 2C, the first outer forceps arm 112 has a narrow fold defining a groove, pocket, or receptacle 118 facing the inner forceps 120 between the gripping end 116a and the pivot end 116b, but the second outer forceps arm 114 has an arcuate, thin blade edge 170 facing the inner forceps 120 between the gripping end 116a and the pivot end 116b. In complementary fashion, the first inner forceps arm 122 has an arcuate, thin blade edge 128 facing the outer forceps 110 between the gripping end 126a and the pivot end 126b, but the second inner forceps arm 124 of the inner forceps 120 has a narrow fold defining a groove, pocket, or receptacle facing the outer forceps 110 between the gripping end 126a and the pivot end 126b. When it is desired to use the bifurcated forceps 100 as a single forceps, the blades 128 snap into the receptacles 118 to temporarily lock the arms 112 and 122 together and the blade 170 of the second outer forceps arm 114 snaps into the receptacle of the second inner forceps arm 124 to temporarily lock the arms 114 and 124 together so that the bifurcated forceps 100 may be used as a single forceps, as shown in FIGS. 3, 4, and 5.

It is to be understood that the bifurcated forceps is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A bifurcated forceps, comprising a first pair of forceps arms and a second pair of forceps arms, each of the forceps arms having a pivot end and a gripping end, the pivot ends of the first and second pairs of forceps arms being resiliently coupled to each other at the pivot ends, the first and second pairs of forceps arms being biased to an open position in which the gripping ends are separated from each other and resiliently pivotal towards each other in a gripping plane in order to grip an object between the gripping ends, the pivot ends of the two arms in each of the pairs being pivotal around a common pivot axis in a rotational plane orthogonal to the gripping plane, whereby the first pair of forceps arms and the second pair of forceps arms may be rotated to spaced radial positions in order to grip the same object at spaced apart positions, wherein the second pair of forceps arms comprises an inner pair of forceps, the pivot ends of the second pair of forceps arms being physically joined directly to each other, further wherein the first pair of forceps arms comprises first and second arms having their pivot ends on opposite sides of the pivot ends of the inner pair of forceps, the first pair of forceps arms defining an outer pair of forceps, whereby the forceps arms of the inner pair of forceps are constrained to rotate together around the common pivot axis, additionally wherein each of the forceps arms of the outer pair of forceps defines a receptacle, and each of the forceps arms of the inner pair of forceps defines a blade edge, the blade edges of the inner pair of forceps being disposed in the receptacles of the outer pair of forceps to lock the inner and outer pairs together so that the bifurcated forceps may be used as a single pair of forceps to grip an object at a single point.

2. The bifurcated forceps according to claim 1, further comprising a pivot pin extending through the pivot end of both of the pairs of forceps, the pivot pin defining the common pivot axis.

3. The bifurcated forceps according to claim 1, wherein the second pair of forceps arms are equal in length.

4. The bifurcated forceps according to claim 1, wherein the second pair of forceps arms are made of a resilient material.

5. The bifurcated forceps according to claim 1, wherein the second pair of forceps arms are made of spring steel.

6. The bifurcated forceps according to claim 1, wherein the second pair of forceps arms are made of resilient plastic.

7. The bifurcated forceps according to claim 1, wherein the pivot ends of the second pair of forceps arms are joined by welding.

8. The bifurcated forceps according to claim 1, wherein the pivot ends of the second pair of forceps arms are joined by adhesive.

9. The bifurcated forceps according to claim 1, further comprising a sliding pin extending through the forceps arms of the outer pair of forceps, whereby the forceps arms of the outer pair of forceps are constrained to rotate together around the common pivot axis.

10. The bifurcated forceps according to claim 1, wherein the forceps arms of the outer pair of forceps are made of resilient material.

11. The bifurcated forceps according to claim 1, wherein the forceps arms of the outer pair of forceps are made of spring steel.

12. The bifurcated forceps according to claim 1, wherein the forceps arms of the outer pair of forceps are made of resilient plastic.

13. A bifurcated forceps, comprising: an outer pair of forceps; an inner pair of forceps, each of the pairs of forceps having forceps arms having a pivot end and a gripping end, the gripping ends of the inner and outer pairs being resiliently biased to a spaced apart relation, wherein adjacent forceps arms of the inner and outer pairs of forceps define a blade edge and a receptacle, respectively, the blade edges being disposed in the receptacles in order to lock the inner and outer pairs of forceps together, whereby the bifurcated forceps may be used as a single pair of forceps; and a pivot pin extending through the pivot ends of the inner and outer pairs of forceps, the forceps arms of the inner and outer pairs of forceps each being resiliently pivotal towards each other in a gripping plane in order to grip an object between the gripping ends of each of the pairs, the pivot ends of the forceps arms in each of the pairs being pivotal around the pivot pin in a rotational plane orthogonal to the gripping plane, whereby the inner pair of forceps arms and the outer pair of forceps arms may be rotated to spaced radial positions in order to grip the same object at spaced apart positions, wherein the pivot ends of the forceps arms of the outer pair of forceps are disposed on opposite sides of the pivot ends of the inner pair of forceps, the pivot ends of the inner pair of forceps being physically joined to each other.

14. The bifurcated forceps according to claim 13, further comprising a sliding pin extending through the forceps arms of the outer pair of forceps, whereby the forceps arms of the outer pair of forceps are constrained to rotate together.

15. A bifurcated forceps, comprising: a first pair of forceps arms and a second pair of forceps arms, each of the forceps arms having a pivot end and a gripping end, the pivot ends of the first and second pairs of forceps arms being resiliently coupled to each other at the pivot ends, the first and second pairs of forceps arms being biased to an open position in which the gripping ends are separated from each other and resiliently pivotal towards each other in a gripping plane in order to grip an object between the gripping ends, the pivot ends of the two arms in each of the pairs being pivotal around a common pivot axis in a rotational plane orthogonal to the gripping plane, whereby the first pair of forceps arms and the second pair of forceps arms may be rotated to spaced radial positions in order to grip the same object at spaced apart positions, wherein the second pair of forceps arms comprises an inner pair of forceps, the pivot ends of the second pair of forceps arms being physically joined directly to each other, whereby the forceps arms of the inner pair of forceps are constrained to rotate together around the common pivot axis, further wherein the first pair of forceps arms comprises first and second arms having their pivot ends on opposite sides of the pivot ends of the inner pair of forceps, the first pair of forceps arms defining an outer pair of forceps, additionally wherein one of the forceps arms of the outer pair of forceps defines a receptacle and one of the arms of the outer pair of forceps defines a blade edge, and one of the forceps arms of the inner pair of forceps defines a blade edge and one of the forceps arms of the inner pair of forceps defines a receptacle, the blade edge of the inner pair of forceps being disposed in the receptacle of the outer pair of forceps and the blade edge of the outer pair of forceps being disposed in the receptacle of the inner pair of forceps to lock the inner and outer pairs of forceps together so that the bifurcated forceps may be used as a single pair of forceps to grip an object at a single point.

* * * * *